United States Patent [19]

Francis et al.

[11] Patent Number: 4,713,383
[45] Date of Patent: Dec. 15, 1987

[54] TRIAZOLOQUINAZOLINE COMPOUNDS, AND THEIR METHODS OF PREPARATION, PHARMACEUTICAL COMPOSITIONS, AND USES

[75] Inventors: John E. Francis, Basking Ridge; Karl O. Gelotte, Watchung, both of N.J.

[73] Assignee: CIBA-GEIGY Corporation, Ardsley, N.Y.

[21] Appl. No.: 844,447

[22] Filed: Mar. 26, 1986

Related U.S. Application Data

[63] Continuation-in-part of Ser. No. 782,235, Sep. 20, 1985, abandoned, which is a continuation-in-part of Ser. No. 655,831, Oct. 1, 1984, abandoned.

[51] Int. Cl.$^4$ .................. A61K 31/505; C07D 487/04
[52] U.S. Cl. ........................ 514/267; 514/23; 536/55; 544/251
[58] Field of Search ............... 544/251, 115; 514/267, 514/239, 23; 536/55

[56] References Cited

U.S. PATENT DOCUMENTS

| | | | |
|---|---|---|---|
| 3,045,015 | 7/1962 | Miller et al. | 544/251 |
| 3,053,844 | 9/1962 | Miller et al. | 544/251 X |
| 3,850,932 | 11/1974 | Kathawala | 544/251 |
| 4,053,600 | 10/1977 | Hardtmann et al. | 514/267 X |
| 4,087,423 | 5/1978 | Treuner et al. | 544/251 |
| 4,112,096 | 9/1978 | Vogt | 514/267 |
| 4,112,098 | 9/1978 | Vogt | 514/267 |
| 4,124,764 | 11/1978 | Treuner et al. | 544/251 |
| 4,128,644 | 12/1978 | Vogt | 514/267 |
| 4,164,578 | 8/1979 | Vogt | 514/267 X |
| 4,463,007 | 7/1984 | Schlecker et al. | 544/251 X |
| 4,585,772 | 4/1986 | Junge et al. | 514/267 X |

FOREIGN PATENT DOCUMENTS

| | | |
|---|---|---|
| 0023773 | 2/1981 | European Pat. Off. |
| 0080176 | 6/1983 | European Pat. Off. |
| 1670375 | 11/1970 | Fed. Rep. of Germany |
| 0048301 | 1/1983 | German Democratic Rep. ............... 544/251 |

OTHER PUBLICATIONS

Reimlinger, et al., Chem Ber., vol. 108(12), pp. 3799–3806 (1975).
Ried, et al., Chemical Abstracts, vol. 69, 27374m (1968).
Leistner, et al., Chemical Abstracts, vol. 94, 208791g (1981).
Renner, et al., Chemical Abstracts, vol. 94, 132,238j (1981).
Fieser, et al., Reagents for Organic Synthesis, John Wiley & Sons, Inc., New York, pp. 846–847 (1967).
Klaubert, J. Med. Chem., vol. 24, pp. 748–752 (1981).
Bulter, Advances in Heterocyclic Chem., vol. 21, p. 355 (1977).

Primary Examiner—Donald G. Daus
Assistant Examiner—Diana G. Rivers
Attorney, Agent, or Firm—Michael W. Glynn; Irving M. Fishman

[57] ABSTRACT

[1,2,4]triazolo[1,5-c]quinazoline compounds of the formula

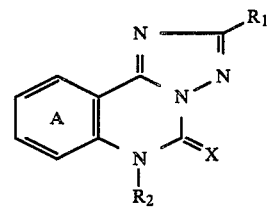

wherein $R_1$ is optionally substituted phenyl, pyridyl, furyl thienyl, dihydro or tetrahydro furanyl or thienyl, pyranyl, or 0-ribofuranosyl; $R_2$ is hydrogen or lower alkyl; X is oxygen or $NR_3$, $R_3$ is as defined in the claims, and ring A is unsubstituted or substituted as set forth in the claims. The compounds wherein X is N—$R_3$ are especially useful as adenosine antagonists and for the treatment of asthma. The compounds wherein X is oxygen are useful as benzodiazepine antagonists and as intermediates in the synthesis of the compounds wherein X is N—$R_3$.

23 Claims, No Drawings

TRIAZOLOQUINAZOLINE COMPOUNDS, AND THEIR METHODS OF PREPARATION, PHARMACEUTICAL COMPOSITIONS, AND USES

FILE HISTORY CROSS REFERENCE

This application is a continuation-in-part of Ser. No. 782,235, filed Sept. 20, 1985, now abandoned, which is a continuation-in-part of Ser. No. 655,831, filed Oct. 1, 1984, now abandoned.

The invention concerns new [1,2,4]triazolo[1,5-c]quinazoline compounds, processes for their preparation, pharmaceutical compositions containing such compounds, and the utility of such compounds and their pharmaceutical compositions.

More particularly, the invention concerns [1,2,4]triazolo[1,5-c]quinazoline compounds having the following formula:

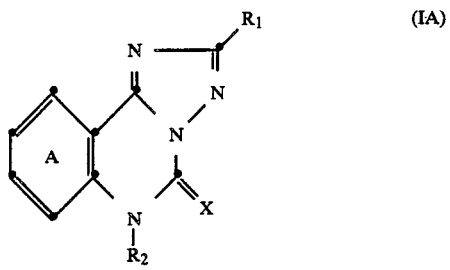

wherein:

$R_1$ represents phenyl or phenyl substituted by lower alkyl, lower alkoxy, hydroxy, halogeno or trifluoromethyl; or a 5 or 6 membered aromatic or partially or totally saturated heterocyclic radical bonded by way of a ring carbon atom, said heterocyclic radical being unsubstituted or substituted by lower alkyl, hydroxy, amino, halogeno or hydroxy-lower alkyl groups;

$R_2$ represents hydrogen, lower alkyl, hydroxy-lower alkyl, lower alkenyl, aryl-lower alkyl, aryl-lower alkenyl, or aryl;

Ring A is unsubstituted or substituted by lower alkyl, lower alkoxy, hydroxy, halogen, trifluoromethyl, nitro, amino, lower alkyl thio, lower alkyl sulfonyl, lower alkyl sulfinyl or aryl-lower alkoxy; and X represent O, S, or N—$R_3$ wherein $R_3$ represents hydrogen, lower alkyl, aryl-lower alkyl, cycloalkyl, lower alkenyl in which the unsaturated bond is separated from the nitrogen atom by at least one saturated carbon atom, lower alkynyl, in which the unsaturated bond is separated from the nitrogen atom by at least one saturated carbon atom, aryl, amino-lower alkyl, lower alkylamino-lower alkyl, di-lower alkylamino-lower alkyl or hydroxy-lower alkyl; salts and tautomers of such compounds, When $R_2$ represents hydrogen, the compounds represented by formula IA may exist in tautomeric form, such as in formula IB:

The term "lower" in connection with organic groups and substituents indicates that the groups and substituents have up to 7 carbon atoms, and preferably up to 4 carbon atoms.

A "heterocyclic radical" refers to an aromatic or non-aromatic heterocyclic ring containing 5 or 6 members. The rings contain from 1 to 4, preferably 1 to 3, more preferably 1 or 2 heteroatoms selected from N, O and S. More preferably, the rings contain 1 to 4 nitrogen atoms, 1 oxygen atom, 1 sulfur atom, or 1 or 2 nitrogen atoms and 1 oxygen or sulfur atom.

"Aryl" refers to an aromatic heterocyclic radical as defined above or to phenyl.

Aryl groups may be further substituted by one or more additional groups such as, for example, lower alkyl, halogeno, hydroxy, nitro, amino, and amino substituted by one or more lower alkyl, or aryl groups.

"Cycloalkyl" contains 3 to 20, preferably 5, 6, 7 or 8, and most preferably 6 members. Cycloalkyl groups may be further substituted by one or more additional groups such as, for example, lower alkyl, or aryl groups.

A lower alkyl group may be unsubstituted or substituted and is, for example, methyl, ethyl, propyl, isopropyl, n-butyl, tert-butyl, pentyl, neopentyl, isopentyl, or heptyl. The preferred group is methyl.

Some suitable substitutents for lower alkyl groups include halogeno and hydroxy. Some examples of substituted lower alkyl groups include chloromethyl, dibromomethyl, trifluoromethyl, trichloromethyl, and hydroxymethyl.

Lower alkoxy is, for example, methoxy, ethoxy, propoxy, isopropoxy, n-butoxy, tert-butoxy, pentoxy, isopentoxy, hexyloxy and heptyloxy. Methoxy is preferred.

Halogeno is, for example, fluoro, chloro, or bromo, preferably, chloro.

An aromatic heterocyclic radical may be, for example, pyridyl; thienyl; furyl; pyrrolyl; thiazolyl or isothiazolyl; oxazolyl, isothiazolyl, imidazolyl or pyrazolyl; or 1,2,3- or 1,2,4-triazolyl, or tetrazolyl.

A non-aromatic heterocyclic radical may be, for example, pyrrolinyl, pyrrolidinyl, dihydrofuranyl, tetrahydrofuranyl, dihydrothienyl, tetrahydrothienyl, pyranyl, piperidinyl, morpholinyl, pyrazolinyl, thiazolinyl, oxazolinyl, triazolinyl and O-ribofuranosyl.

Aryl lower alkyl is, for example, benzyl, phenylethyl, thenyl, thienylethyl, furfuryl, furylethyl, pyridylmethyl, pyridylethyl, pyrrolylmethyl, pyrrolylethyl, piperidinylmethyl and piperidinylethyl.

Aryl-lower alkenyl is, for example, cinnamyl, 3-(2-, or 3-furyl)-2-propene-1-yl, 3-(2-, or 3-pyrrolyl)-2-propene-1-yl, or 3-(2-, 3- or 4-pyridyl)-2-propene-1-yl.

Alkylthio is, for example, methylthio, ethylthio or isopropylthio.

Alkylsulfonyl is, for example, methylsulfonyl or ethylsulfonyl.

Alkylsulfinyl is, for example, methylsulfinyl or ethylsulfinyl.

A cycloalkyl group may be, for example, cyclopropyl, cyclopentyl, cyclohexyl, cycloheptyl, or cyclooctyl.

Lower alkenyl may be, for example, ethenyl, propenyl or butenyl.

Alkynyl may be, for example, ethynyl or propynyl.

Amino-lower alkyl may be, for example, 2-aminoethyl or 2- or 3-aminopropyl. Lower alkylamino-lower alkyl may be, for example 2-(N-methylamino)-ethyl or 2-(N-ethylamino)-ethyl. Di-lower alkylamino-lower alkyl may be, for example, 2-(N,N-dimethylamino)-ethyl or 2-(N,N-diethylamino)-ethyl.

The claimed compounds may form acid addition salts, preferably pharmaceutically acceptable acid addition salts. The acid addition salts may be inorganic or organic. Examples of inorganic salts include halide salts—such as the chloride and bromide, especially chloride—sulfate, phosphate, and nitrate salts. The organic acids may contain, for example, lower alkyl or aryl groups to which are attached one or more than one carboxylate groups or sulfo groups. Some examples of organic salts include, for example, formate, acetate, propionate, succinate, glycollate, lactate, malate, tartarate, gluconate, citrate, maleate, pyruvate, phenylacetate, salicylate, pamoate, methanesulfonate, toluenesulfonate, fumarate, cinnamate, benzoate, 4-amino benzoate, 4-aminosalicylate, nicotinate, 4-hydroxybenzoate, sulfanilate, cyclohexylsulfamate, benzenesulfonate, naphthalenesulfonate, anthranilate, ethanesulfonate, and hydroxyethanesulfonate salts.

The compounds having formula IA or IB and their pharmaceutically acceptable salts, and especially those wherein X represents O or S, are benzodiazepine especially benzocarbomazepine antagonists. However, those in which ring A is substituted with benzyloxy are benzodiazepine agonists. All of the compounds, especially wherein X is oxygen or sulfur are anxiomodulating agents, the precise effect depending upon whether they are benzodiazepine agonists or antagonists. Specific examples of benzodiazepine antagonists are the oxo compounds of Examples 1–22, 24–27, 40, 47, 51, 52, 57, and 67–70. Specific examples of benzodiazepine agonists are the oxo compounds of Examples 71 and 72.

In addition, these compounds, and especially those wherein X represents an imino or substituted imino group, are adenosine antagonists and may be anti-asthma agents and are central nervous system stimulating agents and may enhance cognitive ability. Adenosine antagonism in the heart, as well as in the vasculature and bronchial smooth muscle is demonstrated by the compound of Example 33.

These utilities manifest themselves in mammals such as human beings when administered orally, intraperitoneally or by inhalation in doses of 0.01 mg/kg to 500 mg/kg body weight, preferably 0.1 to 100 mg/kg, and most preferably 10 to 30 mg/kg.

The invention relates particularly to compounds of the formula IA or IB wherein $R_1$ represents phenyl or phenyl substituted by one to three groups selected from lower alkyl, lower alkoxy, hydroxy, halogeno and trifluoromethyl; or $R_1$ represents a heterocyclic radical bonded by way of a carbon atom, said heterocyclic radical being a five or six membered ring which is aromatic or saturated either partially or totally; the heterocyclic group being unsubstituted or substituted by hydroxy, lower alkyl or halogen; $R_2$ represents hydrogen, lower alkyl, aryl-lower alkyl, lower alkenyl, aryl-lower alkenyl, or aryl; X represents O, S, or N—$R_3^A$ wherein $R_3^A$ represents hydrogen, lower alkyl, aryl-lower alkyl, amino-lower alkyl, lower alkylamino-lower alkyl; and wherein ring A is unsubstituted or substituted by one to three groups selected from lower alkyl, lower alkoxy, hydroxy, halogeno, or trifluoromethyl, and pharmaceutically acceptable salts thereof.

The invention relates more particularly to compounds of formula IA or IB wherein $R_1$ represents phenyl or phenyl substituted by one to three groups selected from lower alkyl, for example methyl or ethyl; lower alkoxy, for example methoxy; hydroxy; halogeno, for example fluoro or chloro; and trifluoromethyl; or by a 5- or 6-membered aromatic heterocyclic radical bonded by way of a ring carbon atom; for example 2- or 3-thienyl; 2- or 3-furyl; 2- or 3-pyrrolyl; 2-, 3-, or 4-pyridyl; 3- or 4-pyrazolyl, or 2- or 4-(imidazolyl); said aromatic heterocyclic radical being unsubstituted or substituted by hydroxy; by lower alkyl, for example methyl or ethyl; or by halogeno, for example fluoro or by chloro; wherein $R_2$ represents hydrogen or lower alkyl, for example methyl; wherein X represents O, especially when $R_1$ represents phenyl or substituted phenyl; or X represents N—$R_3^B$ wherein $R_3^B$ represents hydrogen, lower alkyl, for example methyl or ethyl, especially when $R_1$ represents an aromatic heterocyclic group or a substituted aromatic heterocyclic group; and wherein ring A is unsubstituted or substituted by one to three groups selected from halogeno, for example 8- or 9-fluoro, 8- or 9-chloro, or 7,9-dichloro; or lower alkyl; for example 8- or 9-methyl, and pharmaceutically acceptable salts thereof.

The invention relates most particularly to compounds of formula IA or IB wherein $R_1$ represents phenyl or phenyl substituted by halogeno especially in the ortho or meta positions, particularly fluoro or chloro; or furyl especially 2-furyl; wherein $R_2$ represents hydrogen; wherein X represents oxygen especially when $R_1$ represents phenyl substituted by halogeno, for example ortho or meta fluoro; or X represents NH, especially when $R_1$ is 2-furyl; and ring A is substituted by halogen in the 8 or 9 position, especially by chloro in the 9 position, and pharmaceutically acceptable salts thereof.

The invention further relates particularly to compounds of formula IA or IB wherein $R_1$ is phenyl or phenyl substituted by 1–3 groups selected from lower alkyl, lower alkoxy, hydroxy, halogeno, and trifluoromethyl; or $R_1$ is a 5 or 6 membered heterocyclic ring which is aromatic, partially saturated or totally saturated, and bound via a carbon atom thereof, the heterocyclic group being unsubstituted or substituted by hydroxyl, lower alkyl, or halogen; $R_2$ is hydrogen, lower alkyl, aryl-lower alkyl, lower alkenyl, aryl-lower alkenyl, or aryl; X is O, S, or N—$R_3^A$ wherein $R_3^A$ is hydrogen, lower alkyl, aryl-lower alkyl, amino lower alkyl, or lower alkylamino-lower alkyl; and ring A is substituted by aryl-lower alkoxy, preferably benzyloxy; and pharmaceutically acceptable salts thereof.

The invention relates more particularly to compounds of formula IA or IB wherein $R_1$ represents phenyl or phenyl substituted by one to three groups selected from lower alkyl, for example methyl or ethyl; lower alkoxy, for example methoxy; hydroxy; halogeno, for example fluoro or chloro; and trifluoromethyl; or by a 5- or 6-membered aromatic heterocyclic radical bonded by way of a ring carbon atom; for example 2- or 3-thienyl; 2- or 3-furyl; 2- or 3-pyrrolyl; 2-, 3-, or 4-pyridyl; 3- or 4-pyrazolyl, or 2- or 4-(imidazolyl); said aromatic heterocyclic radical being unsubstituted or substituted by hydroxy; by lower alkyl, for example methyl or ethyl; or by halogeno, for example fluoro or by chloro; wherein $R_2$ represents hydrogen or lower alkyl, for example methyl; wherein X represents O, especially when $R_1$ represents phenyl or substituted phenyl; or X represents or N—$R_3^B$ wherein $R_3^B$ represents hydrogen, lower alkyl, for example methyl or ethyl, especially when $R_1$ represents an aromatic heterocyclic group or a substituted aromatic heterocyclic group; and wherein ring A is substituted by one to three, preferably one, aryl-lower alkoxy groups, preferably benzyloxy; and pharmaceutically acceptable salts thereof.

The invention relates most particularly to compounds of formula IA or IB wherein $R_1$ represents phenyl or phenyl substituted by halogeno especially in the ortho or meta positions, particularly fluoro or chloro; or furyl especially 2-furyl; wherein $R_2$ represents hydrogen; wherein X represents oxygen especially when $R_1$ represents phenyl substituted by halogeno, for example ortho or meta fluoro; or X represents NH, especially when $R_1$ is 2-furyl; and ring A is substituted by aryl-lower alkoxy, especially benzyloxy, in the 8 or 9 position, especially the 9 position; and pharmaceutically acceptable salts thereof.

The invention is especially related to the specific compounds mentioned in the examples.

The compounds of the present invention can be prepared by methods known in the prior art. For example, compounds having formula IA or IB wherein X=O or S may be prepared by:

(a) treating a compound having formula II

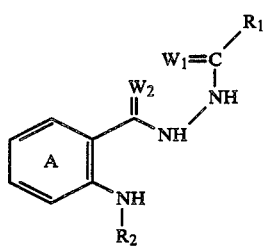

wherein $W_1$ and $W_2$ independently represent O or NH with ammonia and with a reactive derivative of carbonic thiocarbonic or iminocarbonic acids such as phosgene, diethylcarbonate, thiophosgene, trichloromethyl chloroformate, ethyl carbamate, urea, cyanamide, and guanidine, the last two agents resulting in the analogous compounds wherein X is NH.

(a') treating a compound having formula III:

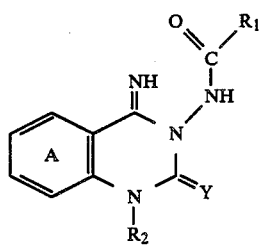

wherein Y represents O or S with a base;

(a1) treating a compound having formula IV

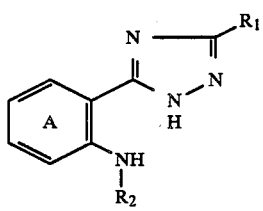

with a reactive derivative of carbonic thiocarbonic or iminocarbonic acid as defined in (a) above; however, the use of cyanamide or guanidine as the reactive derivative result in the analogous compounds wherein X is NH; or (a2) where $R_2$ is hydrogen, treating a compound having formula V

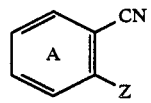

wherein Z represents isocyanato or isothiocyanato; —NHC(=O)O-lower alkyl or —NHC(=S)O-lower alkyl; or —NHC(=O)N-di-lower-alkyl or NHC(=S)N-di-lower-alkyl with a hydrazide having formula VI:

(a3) where $R_2$ represents hydrogen, by treating a compound having formula VII:

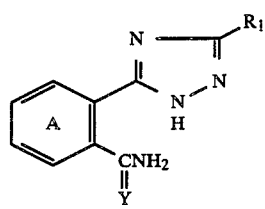

wherein Y represents O with an oxidizing agent followed by ring closure.

(a4) where X is oxo, hydrolyzing the corresponding 5-halo, 5-lower alkoxy, or 5-aryl lower alkoxy compounds having formula IB.

Compounds having formula IA or IB wherein X represents $NR_3$, $NR_3^A$, or $NR_3^B$ may be prepared by:

(b1) when $R_2$ represents hydrogen, displacing a halogen from 5-halo-[1,2,4]triazolo[1,5-c]quinazolines with ammonia or with an amine having the formula $R_3NH_2$, $R_3^ANH_2$ or $R_3^BNH_2$; or (b2) when $R_2$ represents hydrogen, displacing a 5-mercapto (or 5-alkylmercapto) group from a 5-mercapto (or 5-alkylmercapto)-[1,2,4]triazolo[1,5-c]quinazoline with ammonia or with an amine having the formula $R_3NH_2$, $R_3^ANH_2$, or $R_3^BNH_2$; or (b3) treating a compound having formula VIII:

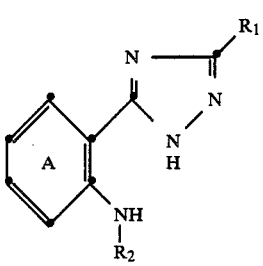

with a cyanogen halide followed by cyclization; or treating a compound of formula VIII with cyanamide or guanidine; or (b4) when X=NH, cyclizing a compound having formula IX:

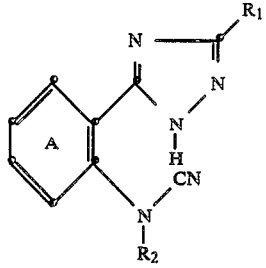

(b5) when X=NH, treating a compound having formula V wherein Z represents N(R$_2$)CN with a hydrazide having formula VI or (b5') doubly cyclizing a compound having formula X:

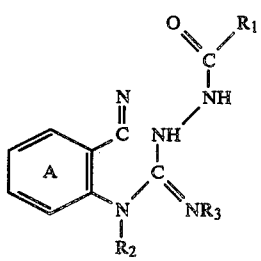

or (b6) treating a compound having formula XI

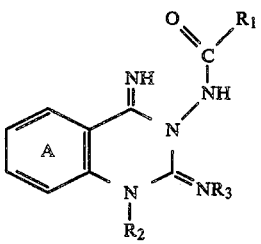

with ammonia; or (b7) treating a compound having formula IB wherein XH represents halogeno such as —Cl, —Br, or —I, or —SCN with ammonia or an amine having the formula H$_2$NR$_3$, H$_2$NR$_3{}^A$, or H$_2$NR$_3{}^B$ or, in any case, (c) by converting one claimed compound into another or by converting a salt into a claimed compound or a claimed compound into a salt.

or (d) treating a compound of Formula XII

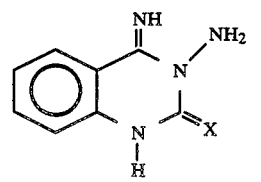

with a compound of formula XIII

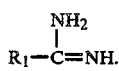

The starting compound of formula XII is prepared by reacting a compound of formula XIV

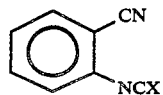

with hydrazine in the presence of an inert solvent such as tetrahydrofuran.

Process a

The base is typically an organic base, preferably a tertiary amine, e.g. pyridine or triethylamine; however, ammonia is also quite suitable.

The source of ammonia may be, for example, a carbamate, such as a lower alkyl carbamate, for example methyl or ethyl carbamate or ammonium carbonate. Reactions may be run with or without an inert solvent at atmospheric or supraatmospheric pressures, for example, in a sealed tube.

The reactive derivatives of carbonic or thiocarbonic acid include esters, amides and anhydrides of carbonic and thiocarbonic acid, such as, for example, phosgene, diethylcarbonate, thiophosgene, trichloromethyl chloroformate, ethyl carbamate or urea.

The source of ammonia may be the same as the reactive derivative of carbonic or thiocarbonic acid, for example a lower alkyl carbamate such as ethyl carbamate.

When W$_1$ and W$_2$ represent NH, II is prepared from an anthranilonitrile and a hydrazidine of the formula

or a hydrazidine of anthranilic acid and a nitrile of the formula R$_1$CN. When W$_1$ represents NH and W$_2$ represents O, II is prepared from an anthranilic hydrazide and a nitrile of the formula R$_1$CN. When W$_1$ represents O and W$_2$ represents NH, II is prepared from a hydrazidine of an anthranilic acid and an acid halide of the formula R$_1$COCl or R$_1$COBr or an anhydride of the formula (R$_1$CO)$_2$O.

Process a'

The source of the ammonia and the reaction conditions are generally the same as those described under process a, above. The starting material is believed to be an intermediate in the reaction of V with R$_1$CONHNH$_2$: The preferred base is a tertiary amine such as triethylamine.

Process a1

The compound having formula IV may be produced according to the method of Potts et al, J. Org. Chem., 35, 3448 (1970). They may also be prepared by treating a reactive intermediate of an anthranilic acid, such as an isatoic anhydride, with a hydrazidine of the formula

or by reacting a thioamide of the formula

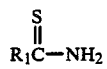

with an anthranilic acid hydrazide. The reactive derivatives of carbonic thiocarbonic or iminocarbonic acid and the general reaction conditions are those described under process a.

Process a2

The reaction takes place preferably in a solvent, such as an ether solvent, for example dioxane or an alcohol solvent, for example 2-methoxyethanol, or a liquid amide, for example, dimethylacetamide.

When Z represents isocyanate or isothiocyanate; or —NHC(=O)O lower alkyl or —NHC(=S)O lower alkyl, the reaction may be conducted in the presence of a base such as a tertiary amine, for example trimethylamine, triethylamine, or ammonia and, especially, tripropylamine. The compounds having formula V wherein Z represents isocyanato and isothiocyanato may be converted into the corresponding compounds wherein Z represents —NHC(=O)O-lower alkyl and —NHC(=S)O-lower alkyl, respectively, by treatment with a lower alkanol such as ethanol. Lower alkyl is preferably methyl or ethyl.

The compounds having formula V wherein Z represents —NH(C=O)O-lower alkyl or —NH(C=S)O-lower alkyl may also be formed by treating an o-aminobenzonitrile with lower alkyl chloroformate or thiochloroformate, for example ethyl chloroformate or ethyl thiochloroformate.

The compounds having formula V wherein Z represents NHC(=O)N-di-lower-alkyl or NHC(=S)N-di-lower alkyl may be formed by treating the appropriate O-isocyanatobenzonitrile or O-isothiocyanatabenzonitrile with a di-lower-alkylamine such as diethylamine.

The preferred solvents when Z represents isocyanato or isothiocyanato are ether solvents, especially dioxane, and more preferably amide solvents, especially 1-methyl-2-pyrrolidinone. The preferred solvents when XH represents —NHC(=O)O-lower alkyl or —NHC(=S)O-lower alkyl; or NHC(=O)N-di-lower alkyl or NHC(=S)N-di-lower alkyl are alcohol solvents, especially 2-methoxyethanol, and more preferably amidic solvents such as 1-methyl-2-pyrrolidinone and dimethylacetamide. The reaction is preferably conducted at temperatures of 0° to 250° C., preferably 20° to 150° C.

Process a3

The oxidizing agent may be, for example, lead tetraacetate or a hypohalite. The hypohalite is preferably an alkali metal hypohalite such as sodium hypochlorite or sodium hypobromite. The amide function is believed to undergo the first stage of the Hofmann reaction (Ber. 14, 2725 (1881), forming the isocyanate which then reacts with the free NH of the triazole.

Process a4

A 5-halo, lower alkoxy or aryl lower alkoxy substituted [1,2,4]triazolo[1,5-c]quinazoline is hydrolyzed. The hydrolysis is preferably effected by base, for example aqueous sodium hydroxide.

The 5-halo compounds may be prepared by reacting a compound of formula 1A wherein X represents O with a reactive halide such as phosphoryl chloride, phosphorous pentachloride, or preferably phenylphosphonic dichloride, with or without an inert solvent.

The 5-lower alkoxy or 5-aryl-alkoxy compounds may be prepared from the 5-halo compounds by treatment with the appropriate alcohol in the presence of base.

Process b1 and b2

A 5-halo, 5-mercapto or 5-alkylmercapto substituted [1,2,4]triazolo[1,5-c]quinazoline is displaced by ammonia or substituted ammonia to form compounds having formula IA wherein X represents NH, NR$_3$, NR$_3$A, or NR$_3$B. The mercapto group may be substituted by lower alkyl, for example a methyl group, by reaction of the 5-mercapto compound with methyl chloride in the presence of a base such as sodium hydride.

Process b3

The cyanogen halide may be, for example, cyanogen chloride or cyanogen bromide. Cyanogen bromide is preferred. A suitable base may be added to neutralize the hydrohalide formed during the reaction. The cyclization preferably occurs in situ as in process b4.

Process b4

This step describes the cyclization of the suspected intermediates from process b3. The reaction may be catalyzed by acid, such as mineral acids (for example, hydrochloric acid) or base such as a trialkylamine.

Process b5

This step is analogous to process a2. The o-cyanimidobenzonitriles are described by Wentrup in Tetrahedron, 27, 367 (1971) and by Bedford et al. in J. Chem. Soc., 1633 (1959).

Process b5'

This process is believed to be an intermediate step in process b5, of which a compound of formula X wherein R$_3$ represents H is believed to be an intermediate.

Process b6

Process b6 is equivalent to process a'. The starting material is believed to be an intermediate in the cyclization of the compound having formula X wherein R$_3$ represents H.

Process b7

The compound having formula IB wherein XH represents —SCN may be treated with ammonia or an amine H$_2$NR$_3$, H$_2$NR$_3$A or H$_2$NR$_3$B in a polar, aprotic solvent, preferably at or near room temperature. The 5-SCN compounds may be prepared from the corresponding 5-thione by treatment of the 5-thione with cyanogen bromide in the presence of a base such as, for example, sodium hydride.

Process c

One claimed compound may be converted into another claimed compound. For example, the 5-thiono compounds may be converted into the 5-oxo compounds by treatment with a hypohalite salt such as sodium hypochlorite or sodium hypobromite. The 5-imino or substituted imino compounds may be hydrolyzed to the corresponding 5-oxo compound with aqueous acid. Compounds 1A wherein R$_2$ represents H and X represents O may be converted to compounds wherein R$_2$ represents lower alkyl, for example by reaction with an alkyl halide in the presence of base, such as sodium alkoxide, in an inert solvent, such as dimethyl sulfoxide.

In the above-described preparations of the compounds of the invention, the reactions are conducted under standard conditions. For example, the reaction mixtures may be cooled or heated to appropriate temperatures, appropriate solvents and catalysts may be added, and the reactions may be conducted under an inert atmosphere.

The claimed salts and claimed neutral compounds are interconvertable. For example, acid addition salts may be converted into neutral compounds by treatment with an appropriate base, and neutral compounds may be converted into the corresponding acid addition salt by treatment with the corresponding acid.

The starting materials for the preparations of the compounds of the invention are either known or may be prepared by methods known in the art.

The compounds of formula IA or IB are formulated into pharmaceutical compositions comprising an effective amount of the triazoloquinazoline compounds of formula IA or IB or a salt thereof in combination with conventional excipients or carriers suitable for either enteral or parenteral, such as oral, bronchial, rectal or intravenous administration. Preferred are tablets, dragees and gelatin capsules comprising the active ingredient together with (a) diluents, e.g., lactose, dextrose, sucrose, mannitol, sorbitol, cellulose, calcium phosphates and/or glycine, (b) lubricants, e.g. silica, talcum, stearic acid, its magnesium or calcium salt and/or polyethyleneglycol; for tablets also, (c) binders, e.g., magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures and/or, (e) absorbents, colorants, flavors and sweeteners. Dragee or tablet cores may be provided with suitable coatings, which may be resistant to gastric juices. Coating solutions are, for example, concentrated aqueous sugar solutions, which may contain gum arabic, polyvinylpyrrolidone, polyethylene glycol, talcum and/or titanium dioxide. Resistant coatings are obtained with lacquer solutions in organic solvents, such as shellac, acetylcellulose phthalate or hydroxypropylmethylcellulose phthalate in ethanol and the like. Dyestuffs or pigments may be added for identification of brand name and dose. Capsules are either made from hard gelatin, or they are soft, closed capsules made from gelatin and a softener, e.g., glycerin or sorbitol. The hard capsules contain either uncompressed powder mixtures, e.g. those mentioned under (a) and (b), or granulates similar to those used for tablets. In the soft capsules said active ingredients are preferably dissolved or suspended in suitable liquids, such as fatty oils, paraffins or polyethylene glycols. Suppositories are advantageously solid, fatty emulsions or suspensions, containing the active ingredient, for example, in natural or synthetic triglycerides, paraffins, waxes and/or polyethylene glycols.

Compositions for parenteral administration are preferably aqueous solutions or suspensions of said active substances, but also oily solutions or suspensions thereof, e.g., in natural or synthetic fatty oils, such as sesame oil or ethyl oleate, in suitable ampules.

Bronchial compositions are preferably aerosol sprays and may be administered from a dispenser such as is described in U.S. Pat. Nos. 4,292,966, 4,174,712, and 4,137,914. The active ingredient is mixed with a propellant such as a hydrocarbon, chlorofluorocarbon mixture, or carbon dioxide.

Said compositions may be sterilized and/or contain adjuvants, such as preserving, stabilizing, wetting or emulsifying agents, solution promoters, salts for regulating the osmotic pressure and/or buffers. They may also contain other therapeutically valuable substances, and are prepared according to conventional mixing, granulating or coating methods respectively. They may contain from about 10 to 95%, preferably from about 20 to 70% of the active ingredient. Individual unit dosages thereof for a mammal of about 50–70 Kg weight may contain preferably between about 10 and 200 mg., advantageously about 20 to 100 mg of said active ingredients.

Having generally described the invention, a more complete understanding can be obtained by reference to certain specific examples, which are provided herein for purposes of illustration only and do not limit the claims unless otherwise specified.

EXAMPLE 1

Seven grams of 3-(2-Carbamoylphenyl)-5-(4-chlorophenyl)-1H-1,2,4-triazole are dissolved in dry dimethylformamide (180 ml) at 50° C. Lead tetraacetate (10.4 g) is added under stirring and the reaction mixture is stirred under nitrogen for ten minutes. The reaction mixture is quenched in crushed ice (500 ml) containing concentrated hydrochloric acid (50 ml). The white solid which forms is collected, washed thoroughly with cold water and recrystallized from 2-methoxyethanol to afford 2-(4-chlorophenyl)-[1,2,4]-triazolo[1,5-c]quinazolin-5(6H)one, mp 315°–318°.

The starting material is prepared in the following manner:

A mixture of 1-hydrazinophthalazine hydrochloride (61 g), p-chlorobenzaldehyde (43.4 g) and methanol (1200 ml) is heated at reflux under nitrogen for 18 hours. The mixture is concentrated under water vacuum, stirred several minutes and filtered. The resulting yellow solid is washed with ether (3×300 ml) and the p-chlorophenylhydrazone (121.2 g) collected and used directly in the following reaction:

The p-chlorophenylhydrazone (120 g) is stirred in a mixture of glacial acetic acid (2300 ml) and anhydrous sodium acetate (160.1 g) for several minutes under nitrogen at room temperature. Bromine (26.2 ml) in glacial acetic acid (150 ml) is added dropwise, after which the reaction mixture is stirred at 90° C. for 12 hours, cooled and filtered. The filtrate is concentrated to dryness at reduced pressure. The residual solid is stirred in water (800 ml), neutralized with aqueous sodium hydroxide solution and stirred 18 hours. The product, 3-(4-chlorophenyl)-1,2,4-triazolo[3,4-a]phthalazine, mp 222°–225°, is used without further purification. Recrystallized from ethanol, the pure compound melts at 224°–225°.

To a mixture of sodium methoxide (12.7 g) in ethanol (1500 ml) is added the above triazolophthalazine (66 g) and the reaction mixture heated at reflux under nitrogen for six days. The mixture is concentrated at reduced pressure to 100 ml, diluted with water (1000 ml) stirred for two hours, filtered and then acidified under cooling with aqueous hydrochloric acid to pH 5. The solid 3-(4-chlorophenyl)-5-(2-cyanophenyl)-1H-1,2,4-triazole (50 g) is collected, washed with water and air dried. The material is suitable for the next step but may be further purified by recrystallization from a mixture of ethanol and isopropanol to afford white solid, mp 236°–238°.

The above crude nitrile (5 g) is dissolved in 85% aqueous sulphuric acid (20 ml), stirred at 80° for 90 minutes and quenched in ice-water (400 ml). The precipitate is collected, washed with water, pressed dry on the filter and then washed with ether. The product, 3-(2-carbamoylphenyl)-5-(4-chlorophenyl)-1H-1,2,4-triazole is recrystallized from 2-methoxyethanol to afford the pure amide mp 234–237.

EXAMPLE 2

By the method described in Example 1, 2-phenyl-[1,2,4]triazolo-[1,5-c]quinazolin-5(6H)one, mp 311°–313° after recrystallization from ethanol, is obtained from 3-(2-carbamoylphenyl)-5-phenyl-1H-1,2,4-triazole. The reaction is conducted for one hour at 80° C. The carbamoyl compound, mp 222°–225°, is prepared from 3-phenyl-1,2,4-triazolo[3,4-a]phthalazine (Druey, Ringier, Helv. Chim. Acta 34, 195–210 (1951)) via the nitrile as described in Example 1.

EXAMPLE 3

To a solution of 3-(2-carbamoylphenyl)-5-(3-pyridyl)-1H-1,2,4-triazole (20.5 g) in dry dimethylformamide (600 ml) is added glacial acetic acid (9.4 g) and treated under stirring at 40° C. with lead tetracetate (35 g). The dark red mixture is stirred at 85° for 66 hours under nitrogen, quenched in ice water (2000 ml) and cooled. After 20 hours, the solid is collected, dissolved in hot ethanol, filtered through diatomaceous earth and the ethanol filtrate treated with p-toluenesulphonic acid hydrate (4.7 g). The tosylate salt of 2-(3-pyridyl)-[1,2,4]triazolo[1,5-c]quinazoline-5(6H)one is precipitated with dry ether, mp 268°–271°. Evaporation of the aqueous mother liquor followed by continuous ether extraction yields a second crop of less pure material.

The starting amide, mp 248°–250° after recrystallization from 2-methoxyethanol, is prepared from 3-(3-pyridyl)-1,2,4-triazolo[3,4-a]phthalazine (Haase, Biniecki, Chem. Abstracts 61, 3103b (1964)) via the nitrile as outlined in Example 1, except that the nitrile and amide are isolated at neutral pH.

EXAMPLE 4

To a mixture of 2-(4-chlorophenyl)-[1,2,4]triazolo[1,5-c]quinazolin-5(6H)one (6 g) in dry dimethylsulphoxide (150 ml) is added sodium methoxide (1.3 g). The mixture is heated under nitrogen for one hour at 85° and methyl iodide (1.3 ml) in dimethyl sulphoxide (10 ml) added. A white solid forms rapidly. The reaction mixture is heated three hours longer, cooled and poured into ice water (800 ml). The precipitated white solid is washed with water, air dried (7.2 g) and recrystallized from dimethylacetamide twice to afford pure 2-(4-chlorophenyl)6-methyl-[1,2,4]triazolo[1,5-c]quinazolin-5(6H)one, mp 323°–325°.

EXAMPLE 5

By the same method described in Example 4, 2-phenyl-[1,2,4]triazolo[1,5-c]quinazolin-5(6H)one is converted to the 6-methyl compound in quantitative yield, crude, and then purified by recrystallization from tetrahydrofuran, mp 231°–234°.

EXAMPLE 6

A mixture of 2-phenyl-[1,2,4]triazolo[1,5-c]quinazolin-5(6H)one (10.4 g) in dry dimethylformamide (150 ml) are treated with 57% sodium hydride in oil dispersion (1.8 g), warmed to 100° under nitrogen and after ten minutes treated with trans-cinnamyl bromide (7.7 g) in dimethylformamide (75 ml) dropwise over twenty minutes. The mixture is stirred four hours at 65° under nitrogen, cooled and quenched in ice-water. The crude precipitated product is recrystallized from dimethylacetamide and then dimethylsulphoxide to afford the pure 6-trans-cinnamyl derivative, mp 167°–169°.

EXAMPLE 7

A mixture of 2-phenyl-[1,2,4]triazolo[1,5-c]quinazolin-5(6H)one (13 g) in dry dimethylformamide (100 ml) is treated with 57% sodium hydride in oil dispersion (2.05 g) and stirred for two hours under nitrogen. To the clear solution is added potassium iodide (0.2 g) followed by sodium hydride in oil dispersion (2.05 g) and then 3-β-picolyl chloride (8.3 g) added little by little with the temperature of the flask raised to 50°. The mixture is stirred under nitrogen at 50° for twenty hours, poured into crushed ice (600 g) and the white solid collected, washed with water and taken up in boiling ethanol (400 ml). It is filtered and the filtrate made acidic to pH 2 with methane-sulphonic acid. The crude salt is recrystallized from ethanol and then suspended in a mixture of ether (100 ml) and 0.5N sodium hydroxide solution. The free base is collected and purified by recrystallization from isopropanol to afford the pure 6-(3-picolyl) derivative, mp 202°–204°.

EXAMPLE 8

A solution of 2-(3-pyridyl)-[1,2,4]triazolo[1,5-c]quinazolin-5(6H)one p-toluenesulphonate (7.3 g) in dry dimethylsulphoxide (60 ml) is treated with 57% sodium hydride in oil dispersion (1.4 g), the mixture heated under nitrogen at 60° for one hour and then treated with methyl iodide (2.4 g). After stirring under nitrogen for 24 hours at 60°, the mixture is quenched in ice water (500 ml) and the precipitate collected, washed with water and air dried. It is suspended in methanol (400 ml), acidified with p-toluene sulphonic acid to pH 4, and the salt precipitated by addition of dry ether. The crude salt is suspended in 2N sodium hydroxide solution, collected, washed with aqueous sodium thiosulphate, water, ethanol and then again converted to the tosylate salt. The salt is recrystallized from ethanol to afford the pure 6-methyl derivative as the tosylate salt, mp 217°–219°.

EXAMPLE 9

A mixture of 1-(2-aminobenzoyl)-2-(isonicotinimidoyl)hydrazine (15 g) and ethyl carbamate (300 g) is stirred under nitrogen with a water separator in the system at an outside temperature of 210° for 4.5 hours, during which time approximately 90 ml of liquid are collected. The residual material, which hardens to a solid during cooling, is stirred at 60° in water (500 ml) for one hour, collected, stirred vigorously with ethyl acetate (500 ml) and again collected. The crude solid is then dissolved in water, made alkaline to pH 13 with sodium hydroxide, filtered and neutralized with acid. The precipitated product is suspended in 2-methoxyethanol (200 ml), acidified with p-toluenesulphonic acid and treated with ether. The precipitated salt is purified via conversion to the free base, reformation of the tosylate salt and recrystallization from methanol to afford pure 2-(4-pyridyl)-[1,2,4]triazolo[1,5-c]quinazolin-5(6H)one p-toluenesulphonate, mp 271°-274°.

The starting material is prepared in the following way: 4-Pyridylhydrazidine (16 g) is mixed with isatoic anhydride (16.3), dry pyridine (200 ml) added and the reaction mixture stirred at room temperature overnight under nitrogen. The precipitate is collected, washed with tetrahydrofuran (50 ml), dry ether (500 ml) and air dried to afford the product, mp 231°-235°. Addition of petroleum ether (1000 ml) to the mother liquor gives a second crop mp 221°-224°.

EXAMPLE 10

By the same route described in Example 9, 3-pyridylhydrazidine is treated with 5-chloroisatoic anhydride in 90% yield and the product, mp 189°-193°, condensed with ethylcarbamate to produce 9-chloro-2-(3-pyridyl)-[1,2,4]triazolo[1,5-c]quinazolin-5(6H)one, as the p-toluenesulphonate salt, mp 320°-322°.

EXAMPLE 11

A mixture of 3-(2-amino-3,5-dichlorophenyl)-5-phenyl-1H-1,2,4-triazole (6 g) and ethylcarbamate (50 g) is heated under nitrogen at 195° for 6 hours after which it is cooled to 80°, poured into water (1000 ml) and stirred 16 hours. The product is collected, washed with water, then methanol (300 ml) and air dried. The crude material is recrystallized from 12:1 2-methoxyethanol-water to afford pure 7,9-dichloro-2-phenyl-[1,2,4]triazolo[1,5-c]quinazolin-5(6H)one, mp 309°-311°.

The starting triazole is prepared as follows:

Benzamidine hydrochloride (25 g) is dissolved in methanol (100 ml) and treated with 50% aqueous sodium hydroxide (13 g). The salt is filtered off and the solution added to 2-amino-3,5-dichlorobenzoic acid hydrazide (26 g) in toluene (300 ml). The reaction mixture is refluxed for 60 hours under nitrogen in an apparatus containing a water separator. The liquid which separates is removed and fresh toluene added to the mixture during this period. The mixture is concentrated at reduced pressure to 75 ml and treated with petroleum ether (300 ml). The white product is collected and recrystallized form methanol to afford the pure product, mp 235°-238°.

EXAMPLE 12

By the method described in Example 11, 3-(2-amino-5-chlorophenyl)-3-(2-pyridyl)-1H-1,2,4-triazole is converted to 9-chloro-2-(2-pyridyl)-[1,2,4]triazolo[1,5-c]quinazolin-5(6H)one, mp>340°, in 88% yield. The starting triazole is prepared in the following manner: A mixture of 5-chloroisatoic anhydride (12 g), 2-pyridylhydrazidine (8.3 g) and pyridine (150 ml) is stirred under nitrogen over 20 hours, ether (200 ml) added and the product collected (14.3 g) mp 230°-232°. This intermediate 1-(2-amino-5-chlorobenzoyl)-2-picolinimidoyl-hydrazine is placed in a mixture of diphenyl ether and biphenyl (3:1 ratio) (150 ml), stirred under nitrogen at 180° for 5 hours, cooled and treated with hexane (200 ml). The product is collected and the triazole obtained, mp 207°-209° after recrystallizaiton from ethanol.

EXAMPLE 13

A suspension of 3-(2-amino-5-chlorophenyl)-5-phenyl-1H-1,2,4-triazole (7 g) in dry dioxane (100 ml) is treated with trichloromethyl chloroformate (5.1 g) and stirred one-half hour under nitrogen at room temperature. Triethylamine (2.62 g) is added and stirring is continued 18 hours. The reaction mixture is then heated one hour at reflux, cooled and the solid collected, washed with ether, then water, and finally suspended and stirred in water vigorously for one-half hour. The product mp>340° is pure 9-chloro-2-phenyl-[1,2,4]triazolo[1,5-c]quinazolin-5(6H)one. The starting triazole, is prepared in the following manner:

Benzamidine free base is generated in ethanol (110 ml) from the hydrochloride (4.64 g) as described in Example 11 and added to a solution of 2-amino-5-chlorobenzoic acid hydrazide (5.0 g) in 9:1 chlorobenzene-ethanol (200 ml) in an apparatus equipped with a water separator. The reaction mixture is refluxed under nitrogen for four hours, during which time 130 ml of liquid are removed and fresh chlorobenzene is added to replace the volume. The mixture is cooled, ether (200 ml) added and the product collected, washed with ether and air dried. The triazole, mp 254°-255°, is analytically pure.

EXAMPLES 14-21

By the same method as described in Example 13, compounds having formula IA wherein $R_2$ represents H and X represents O are prepared from the required 3-(2-aminophenyl)-5-substituted-1H-1,2,4-triazoles, prepared from the required amidine and 2-amino-5-chlorobenzoic acid hydrazide:

| No. | Substituents on ring A | $R_1$ | mp | Starting Triazole mp |
|---|---|---|---|---|
| 14 | 9-Cl | 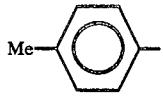 | >320° | >300° |
| 15 | 9-Cl |  | >320° | 254-257° |
| 16 | 9-Cl | 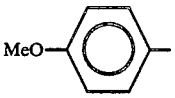 | >320° | 217-219° |
| 17 | 9-Cl | 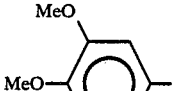 | >290° | 243-248° |
| 18 | 9-Cl | 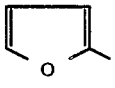 | >340° | 236-237° |
| 19 | 9-Cl | 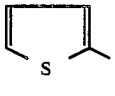 | >330° | 250-251° |
| 20 | 9-Cl | 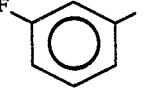 | >320° | 260-263° |

-continued

| No. | Substituents on ring A | R₁ | mp | Starting Triazole mp |
|-----|------------------------|-----|---------|----------------------|
| 21  | 9-Cl                   | F₃C—⟨ ⟩— | 334–336° | 215–217° |

EXAMPLE 22

As described in Example 13, 3-(2-Amino-5-chlorophenyl)-5-(2-fluorophenyl)-1H-1,2,4-triazole is converted to 9-chloro-2-(2-fluorophenyl)-[1,2,4]triazolo[1,5-c]quinazolin-5(6H)one, mp > 360°. The triazole is prepared in the following manner:

A mixture of 2-fluorobenzamide (6.0 g) and 2,4-bis(4-methoxyphenyl)-1,3-dithia-2,4-diphosphetane-2,4-disulphide (8.7 g) in toluene (100 ml) is stirred three hours at reflux, concentrated to dryness at reduced pressure and triturated with dry ether. The solid material obtained is again washed with ether and the combined ether layer filtered through Silica gel and concentrated to form the solid thioamide, used without further purification. The thioamide is combined with 2-amino-5-chlorobenzoic acid hydrazide (7.9 g) in 3:1 diphenyl ether-biphenyl mixture (100 ml) and stirred at 180° under nitrogen for 20 hours. The cooled reaction mixture is diluted with hexane (200 ml) and filtered. The precipitate is separated into 2-(2-amino-5-chlorophenyl)-5-(2-fluorophenyl)-1,3,4-oxadiazole, mp 168°–170° and the desired triazole by high performance liquid chromatography. The triazole obtained has mp 211°–213°.

EXAMPLE 23

Benzoylhydrazine (1.36 g) dissolved in dry dioxane (50 ml) is treated with o-isocyanatobenzonitrile (1.44 g) dissolved in dioxane (20 ml) at 80° for one hour under nitrogen. On cooling, 1.87 g of solid is collected, and on evaporation of the mother liquor, followed by ether treatment, a second crop of solid is obtained. The combined material (2.52 g, mp > 295°) is used directly in the next step. It is placed in a mixture of concentrated ammonium hydroxide (30 ml) and ethanol (120 ml) and heated under reflux for two hours under nitrogen. The solution is partially evaporated at reduced pressure to remove ethanol, cooled and the precipitate collected and washed with water. The product, mp 310°–313°, is identical to 2-phenyl[1,2,4]triazolo[1,5-c]quinazolin-5(6H)one described in Example 2.

EXAMPLE 24

By a similar method to that in Example 23, the intermediate, mp 300°, prepared from 2-isocyanatobenzonitrile and 2-fluorobenzoylhydrazine in 78% yield, is converted to 2-(2-fluorophenyl)-[1,2,4]triazolo[1,5-c]quinazolin-5-(6H)one, mp 326°–329°.

EXAMPLE 25

The intermediate prepared from 2-isocyanato-5-chlorobenzonitrile (6.1 g) and 4-hydroxybenzoylhydrazine (7.0 g) in 53% yield as described in Example 23 is added to a mixture of triethylamine (31 ml), methanesulphonic acid (25 drops) and ethanol (300 ml) and stirred at reflux under nitrogen for two hours. The reaction mixture is concentrated to dryness at reduced pressure, redissolved in ethanol and treated with water. The solid is collected, washed with water and dried under high vacuum to afford pure 9-chloro-2-(4-hydroxy-phenyl)-[1,2,4]triazolo[1,5-c]quinazolin-5(6H)one, mp > 350°

EXAMPLE 26

The intermediate prepared from 2-tetrahydrofuroylhydrazine and 5-chloro-2-isocyanatobenzonitrile in 59% yield by the method described in Example 23, is converted to 9-chloro-2-(2-tetrahydrofuryl)-[1,2,4]triazolo[1,5-c]quinazolin-5(6H)one, mp 239°–243° as described in Example 25.

EXAMPLE 27

The intermediate prepared in 92% yield from N-methylpipecolinic acid hydrazide and 5-chloro-2-isocyanatobenzonitrile as described for Example 23 is converted to 9-chloro-2-[2-(1-methylpiperidyl)]-1,2,4]triazolo[1,5-c]quinazolin-5(6H)one as described in Example 25 and purified as the fumarate salt, mp 274°–276°.

EXAMPLE 28

A suspension of 3-(2-amino-5-chlorophenyl)-5-(2-pyridyl)-1H-1,2,4-triazole, precursor for Example 12, (3.8 g) suspended in methanol (100 ml) is treated with cyanogen bromide (1.5 g) and stirred under nitrogen at reflux for 18 hours. Triethylamine (1.43 g) is added and the suspension stirred at reflux for one hour. It is filtered and the solid washed with methanol and ether, mp > 330°. It is suspended in methanol (100 ml), an equimolar quantity of methansulphonic acid added and the mixture is stirred overnight. The product is collected, washed with methanol and vacuum dried to afford pure 9-chloro-5-imino-2-(2-pyridyl)-5,6-dihydro-[1,2,4]triazolo[1,5-c]quinazoline methanesulphonate, mp 248°–250°.

EXAMPLES 29–36

By the same method as described in Example 28, the following 5-imino-5,6-dihydro-[1,2,4]triazolo[1,5-c]quinazolines were prepared from the requisite triazoles. In some examples, the free base is isolated and in other examples a different salt from the methanesulphonate is prepared.

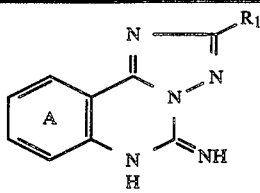

| No. | Substituents on Ring A | R₁ | Acid Addition Salt | mp. |
|---|---|---|---|---|
| 29 | 9-Cl | Me–C₆H₄– | MeSO₃H | 312–315° |
| 30 | 9-Cl | F–C₆H₄– | Me–C₆H₄–SO₃H | 310–312° |
| 31 | 9-Cl | 3,4,5-(MeO)₃–C₆H₂– | MeSO₃H | 278–282° |
| 32 | 9-Cl | C₆H₅– | — | 284–286° |
| 33 | 9-Cl | 2-furyl | MeSO₃H | 275–280° |
| 34 | 9-Cl | F–C₆H₄– | — | >320° |
| 35 | 9-Cl | 2-thienyl | MeSO₃H | 247–252° |
| 36 | 9-Cl | F₃C–C₆H₄– | MeSO₃H | 286–290° |

The 5-methylthio compound used in Examples 37–39 is prepared in the following way:

A mixture of 2-furoic acid hydrazide (15.8 g), 2-cyanophenylisothiocyanate (20.0 g) and dry dioxane (600 ml) is stirred at reflux under nitrogen for one hour. The reaction mixture is concentrated to dryness under reduced pressure, the residue triturated with methanol and the solid collected. This intermediate (32.6 g, mp>300°) is suspended in a mixture of triethylamine (230 ml), ethanol (1800 ml) and methanesulphonic acid (7 ml), stirred under reflux under nitrogen for two hours, concentrated to a thick oil at reduced pressure, taken up in ethanol (300 ml) and stirred until crystallization is complete. The solid, which is crude 2-(2-furyl)-5-mercapto-[1,2,4]triazolo[1,5-c]quinazoline, mp>300°, is used directly in the next step.

To a solution of sodium methoxide (0.83 g) in methanol (20 ml) is added the above mercapto compound (2.01 g), stirred several minutes and then treated with methyl iodide (0.47 ml). A solution forms and on heating one hour at 80° bath temperature, a thick precipitate forms which is further diluted with methanol, cooled and air dried. The solid, mp 188°–190°, is collected, washed with methanol and air dried.

EXAMPLE 37

2-(2-Furyl)-5-methylthio-[1,2,4]triazolo[1,5-c]quinazoline (1.41 g) is placed in a stainless steel pressure vessel with ethanol (200 ml) and 70% aqueous ethylamine (100 ml) and heated to an outside temperature of 150°. It reaches a pressure of 100 p.s.i. and is maintained at that pressure and temperature for 16 hours. It is cooled and the material concentrated to dryness at reduced pressure The residual solid is recrystallized from methanol to afford pure 5-ethylimino-2-(2-furyl)-5,6-dihydro-[1,2,4]triazolo[1,5-c]quinazoline, mp 133°-135°.

EXAMPLE 38

In a similar way to the method of Example 37, 2-(2-furyl)-5-methylthio-[1,2,4]triazole[1,5-c]quinazoline is converted with 40% aqueous methylamine in ethanol to 2-(2-furyl)-5-methylimino-5,6-dihydro-[1,2,4]triazolo[1,5-c]quinazoline, mp 193°-195° after methanol recrystallization.

EXAMPLE 39

As in Example 37, 2-(2-furyl)-5-methylthio-[1,2,4]triazolo[1,5-c]quinazoline is reacted with ammonium hydroxide (200 ml) saturated with ammonia at 0° in the stainless steel pressure vessel at 150° and 220 p.s.i. over six hours to afford 2-(2-furyl)-5-imino-5,6-dihydro[1,2,4]triazolo[1,5-c]quinazoline, mp 282°-285° after methanol recrystallization.

EXAMPLE 40

A mixture of 3-(2-methylaminophenyl)-5-(2-furyl)-1H-1,2,4-triazole (4.8 g), cyanogen bromide (2.17 g) and methanol (150 ml) is heated at reflux under nitrogen for 18 hours. The mixture is filtered hot to remove 600 mg of 2-(2-furyl)-6-methyl-[1,2,4]triazolo[1,5-c]quinazolin-5(6)-one (mp 238.5°-241.5° after 2-methoxyethanol recrystallization). On cooling, a white solid (4.0 g) is obtained, which is taken up in methanol, treated with triethylamine (2.8 ml), heated two hours under reflux, diluted with cold water and collected by filtration. The solid material is recrystallized from 2-methoxyethanol-methanol mixture and then converted to the methanesulphonate salt in methanol with isopropanol added during cooling. The salt is then taken up in water (300 ml) containing a few drops of methanesulphonic acid, filtered free of impurity, evaporated at reduced pressure to a small volume and precipitated by addition of isopropanol. The product is dried under high vacuum at 100° for 18 hours to afford pure 2-(2-furyl)-5-imino-6-methyl-5,6-dihydro-[1,2,4]triazolo[1,5-c]quinazoline methanesulphonate, mp 259°-263°.

The starting material is prepared in the following manner:

2-(Methylamino)benzoic acid hydrazide (Hetter et al, J. prakt. Chem. 111, 36-53 (1925)) (14.5 g) is treated with 2-furanamidine, prepared from 12.9 g of the hydrochloride, as described in Example 13 to give the desired triazole, mp 179°-183°.

EXAMPLE 41

Concentrated aqueous ammonium hydroxide (50 ml) in a stainless steel pressure vessel is saturated with gaseous ammonia at 0° and 5,9-dichloro-2-(2-tetrahydrofuryl)[1,2,4]triazolo[1,5-c]-quinazoline (1.22 g) added. The mixture is heated over six hours at an outside temperature of 150°, cooled and filtered. The precipitate is washed with water and dried under high vacuum to afford pure 9-chloro-5-imino-2-(2-tetrahydrofuryl)-5,6-dihydro-[1,2,4]triazolo[1,5-c]-quinazoline (0.45 g), mp 203°-206°. The starting material is prepared as follows:

A mixture of phosphoryl chloride (45 ml), phosphorous pentachloride (0.3 g) and the product of Example 26 (2.1 g) is stirred at room temperature under nitrogen. After five minutes, pyridine (1.2 ml) is added dropwise. The reaction mixture is gradually heated to 110° over one hour, stirred at 110° for 16 hours, filtered and concentrated at reduced pressure to dryness. The residue is taken up in ethyl acetate, washed with 2N aqueous hydrochloric acid, dried over sodium sulphate and concentrated to dryness. On recrystallization from ethyl acetate, the dichloro compound melts at 150°-152°.

EXAMPLE 42

A mixture of concentrated aqueous ammonium hydroxide (300 ml) saturated with ammonia gas at 0° and 9-chloro-2-(2-furyl)-5-methylthio[1,2,4]triazolo[1,5-c]quinazoline (5.7 g) in a stainless steel pressure vessel is heated at an outside temperature of 150° over 18 hours, during which time the pressure rises to 250 p.s.i. The reaction mixture is cooled and the solid material collected, washed with water and air dried. The 9-chloro-2-(2-furyl)-5-imino-5,6-dihydro-[1,2,4]triazolo[1,5-c]quinazoline thus obtained (2.9 g, mp 269°-271°) is converted to the methanesulphonate salt by dissolution in 2-methoxyethanol (150 ml) followed by methanesulphonic acid (0.66 ml) and dry ether (25 ml) to afford the pure salt identical to that from Example 32.

The starting material is prepared in the following way:

A suspension of 2-amino-5-chlorobenzonitrile (40.6 g) in water (400 ml) is treated dropwise under vigorous stirring under nitrogen with thiophosgene (20.3 ml) and after three hours of vigorous stirring, the isothiocyanate is collected, washed with water, then with cyclohexane (2×100 ml) and dried under vacuum. The isothiocyanate (18.5 g) and 2-furoylhydrazine (28.7 g) dissolved in dioxane are refluxed under nitrogen for one hour, cooled and teated with triethylamine (22.2 ml) and methanesulphonic acid (0.1 ml). After two hours at reflux, the reaction mixture is concentrated to dryness at reduced pressure, suspended in isopropanol (300 ml) and stirred vigorously for one hour. The solid is collected and air dried (13.9 g) and the 9-chloro-2-(2-furyl)-5-thiono-5,6-dihydro-[1,2,4]triazolo[1,5-c]quinazoline thus obtained is used directly in the following step:

A mixture of 9-chloro-2-(2-furyl)-5-thiono-5,6-dihydro-[1,2,4]triazolo[1,5-c]quinazoline (17.7 g), methanol (200 ml) and sodium methoxide (31.4 g) is stirred for 5 minutes at room temperature under nitrogen and then treated dropwise with methyl iodide (3.7 ml). Methanol (200 ml) is added and the reaction mixture stirred at 80° outside temperature under nitrogen for two hours, cooled, and the 9-chloro-2-(2-furyl)-5-methylthio-[1,2,4]triazolo[1,5-c]quinazoline collected, washed with water and air dried, mp 202°-207°.

EXAMPLE 43

As described in Example 42, 2-[2-(N-methylpiperidyl)]-5-methylthio[1,2,4]triazolo[1,5-c]quinazoline is converted to 5-imino-2-[2-(N-methylpiperidyl)]-5,6-dihydro[1,2,4]triazolo[1,5-c]quinazoline, mp 193°-194°. The methylthio compound, mp 142°, is prepared from the mercapto compound in 80% yield which originates from o-cyanophenylisothiocyanate and N-methylpipecolinic acid hydrazide as described in Example 42.

EXAMPLE 44

As described in Example 42, 2-[2-(N-methylpyrrolyl)]-5-methylthio[1,2,4]triazolo[1,5-c]quinazoline is converted to 5-imino-2-[2(N-methylpyrrolyl)]-5,6-dihydro[1,2,4]triazolo[1,5-c]quinazoline, mp 251°-254°. The starting material is prepared as described in Example 42 starting from o-cyanophenylisothiocyanate and N-methylpyrrole-2-carboxylic acid hydrazide.

EXAMPLE 45

A mixture of 2-(2-pyrrolyl)-5-thiono-5,6-dihydro[1,2,4]triazolo[1,5-c]quinazoline (4.28 g), prepared from 5-chloro-2-isothiocyanatobenzonitrile and 2-pyrrolecarbohydrazide as described in Example 39, is placed in a stainless steel pressure vessel with 40% aqueous methylamine saturated at 0° with methylamine gas (225 ml) and heated 6 hours at an outside temperature of 150° C. The reaction mixture is cooled to room temperature and the solid collected, washed with water and air dried. Recrystallization from aqueous methanol, then water affords pure 5-methylimino-5,6-dihydro-2-(2-pyrrolyl)-[1,2,4]triazolo-[1,5-c]quinazoline, mp 220°-221°.

EXAMPLE 46

As in Example 39, 3-furoic acid hydrazide is reacted with 5-chloro-2-cyanophenyl isothiocyanate to produce 2-(3-furyl)-5-mercapto-[1,2,4]triazolo[1,5-c]quinazoline, mp>300°, which is converted to the 5-methylthio compound and thence to 9-chloro-2-(3-furyl)-5-imino-5,6-dihydro[1,2,4]triazolo[1,5-c]quinazoline, purified as the methanesulphonate salt, mp 290°-292°.

EXAMPLE 47

As in Example 13, 3-(2-amino-5-chlorophenyl)-5-(3-furyl)-1H-1,2,4-triazole, obtained by evaporation of the mother liquor from the preparation of the imino compound of Example 46, was converted to 9-chloro-2-(3-furyl)-[1,2,4]triazolo[1,5-c]quinazolin-5(6H)one, mp>350°, after recrystallization from dimethylacetamide-water.

EXAMPLE 48

A mixture of 9-chloro-2-(2-furyl)-5-methylthio(1,2,4]-triazolo[1,5-c]quinazoline (5.7 g) is refluxed with cyclohexylamine (40 ml) under nitrogen for 6 hours. The mixture is cooled and the insoluble solid collected and recrystallized from ethanol to afford pure 9-chloro-5-cyclohexylamino-2-(2-furyl)-[1,2,4]triazolo[1,5-c]quinazoline, mp 158°-160°.

EXAMPLE 49

A mixture of 9-chloro-2-(2-furyl)-5-mercapto[1,2,4]-triazolo[1,5-c]quinazoline (5.6 g) and aniline (40 ml) is stirred at 150° for 66 hours under nitrogen. The mixture is heated on a rotary evaporator under water pump vacuum to remove residual aniline and recrystallized from aqueous ethanol to afford pure 9-chloro-2-(2-furyl)-5-phenylimino-5,6-dihydro-[1,2,4]triazolo[1,5-c]quinazoline, mp 231°-233°.

EXAMPLE 50

As in Example 37, 9-chloro-2-(2-furyl)-5-methylthio[1,2,4]triazolo[1,5-c]quinazoline (1.06 g) is reacted in a stainless steel pressure vessel with isopropylamine (50 ml) at 150° (external temperature) for 6 hours to afford 9-chloro-2-(2-furyl)-5-isopropylimino-5,6-dihydro-[1,2,4]triazolo[1,5-c]quinazoline, which is purified by ethanol recrystallization, mp. 140°-141°.

EXAMPLE 51

A mixture of N-carbethoxyanthranilonitrile (1.9 g), prepared as described by Breukink and Verkade, Rec. trav. Chim. 79, 443 (1960), 2-furoic acid hydrazide (1.26 g), 2-methoxy-ethanol (50 ml) and tri-n-propylamine (1 ml) is heated at reflux under nitrogen for 20 hours. Part of the solvent (30 ml) is distilled off and the mixture allowed to cool. The white crystals are collected, washed with methanol and dried in vacuo, to afford pure 2-(2-furyl)[1,2,4]triazolo[1,5-c]quinazolin-5(6H)one, mp. 338°-343°.

EXAMPLE 52

As described in Example 51, 9-chloro-2-(3-chlorophenyl)-[1,2,4]triazolo[1,5-c]quinazolin-5(6H)one, mp.>350°, (4.2 g) is prepared from N-carbomethoxy-5-chloro-2-aminobenzonitrile (4.2 g) and 3-chlorobenzhydrazide (3.4 g). The urethane starting material is prepared by reacting 2-amino-5-chlorobenzonitrile (15.6 g), methylethylketone (200 ml) and sodium bicarbonate (10 g) with methyl chloroformate (8.4 ml) at 80° for 42 hours under nitrogen. The reaction mixture is cooled, filtered free of inorganic material, concentrated to dryness at reduced pressure and recrystallized from chlorobenzene-cyclohexane mixture to afford the product, mp. 127°-132°.

EXAMPLE 53

As described in Example 52, N-carbomethoxy-5-chloro-2-aminobenzonitrile (4.2 g) is reacted with 2-fluorobenzhydrazide (3.1 g) in 2-methoxyethanol (100 ml) with tri-n-propylamine (0.3 ml) at reflux 24 hours under nitrogen to afford pure 9-chloro-2-(2-fluorophenyl)-[1,2,4]triazolo(1,5-c]quinazolin-5(6H)one identical to the material described in Example 22.

EXAMPLE 54

A mixture of ethyl-N-(2-cyanophenyl)thiocarbamate (3.0 g), 2-furoic acid hydrazide (1.83 g), tri-n-propylamine (2 ml) and 2-methoxyethanol (50 ml) is refluxed under nitrogen for 18 hours. The reaction mixture is concentrated at reduced pressure to a thick oil which crystallizes on treatment with methanol. The solid is identical to the sample of 2-(2-furyl)-5-mercapto-[1,2,4]triazolo[1,5-c]quinazoline prepared as described in Example 39.

The thiocarbamate is prepared by refluxing o-cyanophenylisothiocyanate in excess absolute ethanol overnight under nitrogen. After filtration at room temperature, the filtrate is concentratred to dryness at reduced pressure and the residual solid recrystallized from cyclohexane to afford the thiocarbamate, mp. 87°-89°.

EXAMPLE 55

Gaseous ammonia is bubbled into a solution of 9-chloro-2-(2-furyl)-5-thiocyanato-[1,2,4]triazolo[1,5-c]quinazoline (15 g) in 1,3-dimethylimidazolidone (200 ml) cooled in an ice bath over a one-half hour period. After one hour longer at ambient temperature, the mixture is diluted with water (500 ml) and the solid collected and recrystallized from 2-methoxyethanol with a little water added. After 18 hours drying at 100°/0.2 mm, the pure 9-chloro-5-imino-5,6-dihydro-[1,2,4]triazolo[1,5-c]quinazoline, mp. 279°-280°, is obtained in 70% yield.

The starting material is prepared essentially as described by Vlattas, et al, J. Heterocyclic Chem. 20, 1287 (1983) as follows:

To a heterogeneous suspension of sodium hydride (50% in oil), (790 mg) in dry tetrahydrofuran (40 ml) is added in portions 9-chloro-2-(2-furyl)-5-thiono-5,6-dihydro[1,2,4]triazolo[1,5-c]quinazoline (from Example 39), 5.0 g) in a nitrogen-rich atmosphere. It is stirred two hours under nitrogen, cooled to 0° externally and treated dropwise under nitrogen with a solution of cyanogen bromide (1.75 g) in tetrahydrofuran (15 ml). It is stirred in the ice bath for one-half hour, diluted with water (100 ml) and extracted three times with 100 ml portions of ethyl acetate. The combined organic extracts are filtered, dried over magnesium sulphate and concentrated to dryness at reduced pressure to afford the desired isothiocyanato compound of adequate purity. Recrystallization from 2-methoxyethanol gives the pure sample, mp. 218°–220° C.

EXAMPLE 56

A mixture of N,N-dimethyl-N'-(4-chloro-2-cyanophenyl) urea (1.79 g), 2-furoic acid hydrazide (1.05 g) and 2-methoxyethanol (25 ml) is refluxed under nitrogen for 20 hours. The mixture is cooled and the crystalline 9-chloro-2-(2-furyl)-[1,2,4]triazolo[1,5-c]quinazolin-5(6H)one (2.0 g) collected, washed with water, then methanol and dried in vacuo. The material is identical to the substance obtained in Example 18.

The starting urea is prepared by dissolution of 4-chloro-2-cyanophenylisocyanate (2.7 g) in warm toluene (100 ml) followed by treatment with 17.6% dimethylamine in toluene (20 ml) at room temperature under nitrogen over 20 hours. It is concentrated to dryness at reduced pressure and temperature no higher than 50° to afford 3.2 g of solid material, which is recrystallized from cyclohexane to afford the pure urea, mp. 95°–97°.

EXAMPLE 57

A mixture of N-Carbethoxy-5-nitroanthranilonitrile (2.15 g), 2-fluorobenzhydrazide (1.56 g), tri-n-propylamine (1 ml) and (±)-1-Methoxy-2-propanol (50 ml) is stirred at reflux under nitrogen for 20 hours. It is cooled, treated with methanol (50 ml) and filtered. The white precipitate is washed with methanol and recrystallized from dimethylacetamide ethanol to afford pure 2-(2-fluorophenyl)-9-nitro-[1,2,4]triazolo[1,5-c]quinazolin-5(6H)-one, which melts above 350° C.

EXAMPLE 58

A solution of 9-chloro-5-thiocyanato-2-(2-furyl)[1,2,4]triazolo-[1,5-c]quinazoline (2 g) in 1,3-dimethylimidazolidone (28 ml) is added to tert-butylamine (2 ml). The mixture is stirred for 3 hours under nitrogen, and then is diluted with ethanol (20 ml), and treated with water (20 ml). The resulting precipitate is collected, recrystallized from 2-methoxyethanol, and dried in high vacuum to afford pure 5-tert-butylamino-9-chloro-2-(2-furyl)-[1,2,4]triazolo-[1,5-c]quinazoline, mp above 330° C.

EXAMPLE 59

When tert-butylamine in Example 57 is replaced by ethanolamine, 9-chloro-2-(2-furyl)-5-hydroxyethylamino[1,2,4]triazolo[1,5-c]quinazoline is obtained in the same fashion, mp. 214°–217° C.

EXAMPLE 60

Preparation of 10,000 tablets each containing 50 mg of the active ingredient:

| Formula: | |
|---|---|
| 2-(2-fluorophenyl)-9-chloro[1,2,4]-triazolo[1,5c]quinazolin-5(6H)one. | 500.00 g |
| Lactose | 707.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches, uppers bisected.

EXAMPLE 61

Preparation of 10,000 capsules each containing 20 mg of the active ingredient:

| Formula: | |
|---|---|
| 2-(3-fluorophenyl)-9-chloro[1,2,4]-triazolo[1,5-c]quinazolin-5(6H)one. | 200.0 g |
| Lactose | 1,700.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg each, using a capsule filling machine.

EXAMPLE 62

Preparation of 10,000 capsules each containing 20 mg of the active ingredient:

| Formula: | |
|---|---|
| 2-(2-furyl)-5-imino-9-chloro-5,6-dihydro[1,2,4]triazolo[1,5-c]quinazoline | 200.0 g |
| Lactose | 1,700.0 g |
| Talcum powder | 100.0 g |

Procedure

All the powders are passed through a screen with openings of 0.6 mm. Then the drug substance is placed in a suitable mixer and mixed first with the talcum, then with the lactose until homogeneous. No. 3 capsules are filled with 200 mg each, using a capsule filling machine.

EXAMPLE 63

To a solution of 1.45 g of 5,9-dichloro-2-(2-furyl)[1,2,4]triazolo[1,5-c]quinazoline in dry tetrahydrofuran (150 cc) at 50° is added gaseous methylamine over 40 minutes. The mixture is concentrated to dryness, triturated with water and filtered to afford a white solid. This is recrystallized by dissolution in hot toluene and, after several minutes of heating to remove water by azeotropic distillation, addition of cyclohexane during cooling. Pure 9-Chloro-2-(2-furyl)-5-methylamino[1,2,4]triazolo[1,5-c]quinazoline, mp 166°–168°, is thus obtained.

The starting material is prepared in the following manner:

A mixture of 15 g of 9-chloro-2(2-furyl)[1,2,4]-triazolo[1,5-c]quinazolin-5(6H)one (Example 18) in 275 ml of phenylphosphonic dichloride is heated at 182° to 187° for 24 hours. The excess solvent is distilled off under vacuum and the residue cooled and triturated with 750 ml of methylene chloride. It is heated to reflux and residual starting material removed by filtration. The filtrate is treated with charcoal, filtered through diatomaceous earth, and concentrated to a small volume at reduced pressure. The dichloro compound crystallizes at 0°, mp 242°–242.5° with decomposition.

EXAMPLE 64

When the 5,9-dichloro compound described above is reacted with excess concentrated ammonium hydroxide solution under ice-cooling and the reaction mixture is diluted with water, 9-chloro-2-(2-furyl)-5-imino-5,6-dihydro[1,2,4]triazolo[1,5-c]quinazoline is obtained, mp 276°–278°.

EXAMPLE 65

To a solution of 4.9 g of 2-(5-bromo-2-furyl)-9-chloro-5-thiocyanato[1,2,4]triazolo[1,5-c]quinazoline in 80 cc of tetrahydrofuran is added gaseous ammonia under ice cooling over 1.3 hr. The precipitate which forms is collected washed with tetrahydrofuran, recrystallized from N,N-dimethyl acetamide and dried under high vacuum at 100° to afford pure 2-(5-bromo-2-furyl)-9-chloro-5-imino-5,6-dihydro[1,2,4]triazolo[1,5-c]quinazoline, mp 282°–283°.

The starting material is made in the following manner:

A mixture of 6 g of 5-bromo-2-furoic acid hydrazide (prepared as described by Blomquist and Stevenson, JACS 56, 148 (1934)), 5.8 g of 5-chloro-2-cyanophenyl isothiocyanate and 70 cc of N-methyl pyrrolidone is stirred at 150° under nitrogen over 4 hr, quenched in a mixture of 300 cc of ice-water and 100 cc of isopropanol and the precipitate collected and pressed as dry as possible on the filter. It is dissolved in 150 cc of hot dioxane, filtered, concentrated to about 20 cc, cooled and treated with 100 cc of methanol to afford pure 2-(5-bromo-2-furyl)-9-chloro-5-mercapto[1,2,4]triazolo[1,5-c]quinazoline, mp 273°–276°. The 5-mercapto compound is then converted to the 5-thiocyanato compound as described in Example 55.

EXAMPLE 66

To a slurry of 15.1 g of 3-(2-amino-5-chlorophenyl)-5-(2-furyl)-1,2,4-triazole (intermediate from Example 18) in 300 cc of isopropanol under stirring is added 7.4 cc of 50% aqueous cyanamide followed by a mixture of 3.7 g of concentrated sulfuric acid in 4 cc of water. The mixture is heated under reflux for 6 hr, cooled to room temperature and the pH of the slurry adjusted to 7 by addition of 10% aqueous sodium hydroxide. The mixture is cooled in an ice bath and stirred ½ hr. at 5°. The precipitate is collected, washed with cold anhydrous ethanol and dried at 80° in vacuo for 18 hr.

The crude solid is dissolved in 240 cc of glacial acetic acid at 110°–115°, treated with charcoal and filtered hot through diatomaceous earth. The filtrate is cooled to room temperature, stirred 1 hr. and the solid collected, washed with three 80 cc portions of water, then 40 cc of anhydrous ethanol and dried at 80° under vacuum for 18 hr. to afford pure 9-chloro-2-(2-furyl)-5-imino-5,6-dihydro[1,2,4]triazolo[1,5-c]quinazoline, identical to that described in Example 64.

The starting material can be prepared by an alternate route to that described in Example 13:

Chlorine gas is bubbled through a solution of 47.55 g of 2-(ethoxycarbonylamino)benzonitrile (see Example 51) in 100 cc of N,N-dimethylformamide at such a rate to maintain the internal temperature of 30°±2° under vigorous stirring. When the starting material is no longer present, as shown by HPLC analysis, nitrogen is then bubbled through the stirring mixture for 1 hr and then 200 cc of water are added dropwise under cooling. The product is collected, washed with water and dried at 50°–60° under vacuum for 16 hr. The resulting 5-chloro-2-(ethoxy-carbonylamino)benzonitrile, mp 126°–129° is recrystallized from aqueous ethanol to afford pure material, mp 131°–133°. Fifteen g of this urethane are combined with 8.42 g of 2-furoic acid hydrazide and 75 cc of N-methyl pyrrolidone and stirred at 160° (bath temperature) over 5 hr in an apparatus with a water separator. Some solvent distills over and the solution is cooled and 150 cc of water gradually added as the temperature subsides. At room temperature, the product is collected, washed with 100 cc of water followed by 50 cc of isopropanol, dried at 70°–75° under vacuum over 16 hr. The product, 9-chloro-2(2-furyl)-[1,2,4]triazolo[1,5-c]quinazolin-5(6H)one, is identical to that obtained in Example 18. Sixty grams of this product is stirred in 350 cc of ethylene glycol and treated with a solution of 17.1 g of sodium hydroxide in 55 cc of water. The whole is stirred at reflux for 19 hr, cooled to room temperature and treated with 350 cc of water. The pH of the resulting slurry is adjusted to 6.5 to 7.0 by addition of glacial acetic acid. It is stirred 15 min. longer and the solid collected, washed with three 50 cc portions of water and dried at 80° in vacuo over 16 hr to afford pure 3-(2-amino-5-chlorophenyl)-5-(2-furyl)-1,2,4-triazole identical to the intermediate used in Example 18.

EXAMPLE 67

A mixture of o-fluorobenzhydrazide (350 mg), N-Carbethoxy-5-methoxyanthranilonitrile (500 mg) and N-methylpyrrolidone (9 ml) is heated under nitrogen at 160° for 4 hr. It is cooled, poured into water (60 ml) and the precipitate collected and recrystallized from dimethylformamide-water to afford pure 5,6-dihydro-2-(2-fluorophenyl)-9-methoxy-[1,2,4]triazolo[1,5-c]quinazolin-5(6H) one, mp. 315°–317°.

The N-carbethoxy starting material is prepared in the following manner: A mixture of 5-methoxyanthranilonitrile (Bartlett, Dickel and Taylor, J.A.C.S. 80, 136 (1958), 2.25 g) and ethyl chloroformate (60 ml) is heated under reflux for 20 min. and then concentrated to dryness at reduced pressure. The residue is taken up in toluene (20 ml) hexane (50 ml) added and the precipitate collected, washed with hexane and air dried to afford the pure urethane, mp. 142°–144°.

EXAMPLE 68

When 2-furoic acid hydrazide is substituted for o-fluorobenz hydrazide in Example 67, 5,6-dihydro-2-(2-furyl)-9-methoxy-[1,2,4]triazolo[1,5,c]quinazolin-5(6H) one is obtained, mp. 320°–321°, after recrystallization from dimethylformamide-water mixture.

EXAMPLE 69

A mixture of N-Carbethoxy-5-hydroxyanthranilonitrile (1.5 g), 2-furoic acid hydrazide (0.9 g) and N-methylpyrrolidone (25 ml) is stirred under nitrogen at 160° for 3 hr. Water is added to the cooled mixture and a solid precipitates. It is collected, washed with water, air dried and triturated with hot 5:1 ethyl acetate-ethanol mixture. The insoluble material is recrystallized from dimethylformamide-water mixture to afford pure 5,6-dihydro-2-(2-furyl)-9-hydroxy-[1,2,4]triazolo[1,5-c]quinazolin-5(6H) one, melting above 350°.

The starting N-carboethoxy compound is prepared in the following way: A mixture of 5-hydroxyanthranilonitrile (1 g) and ethyl chloroformate (10 ml) is heated at reflux for 4 hr., concentrated to dryness and taken up in warm ethyl acetate. It is filtered free of starting material and the mother liquor cooled and treated with petroleum ether. The precipitated solid is the desired urethane. The starting anthranilonitrile is prepared by addition of 5-benzyloxy-2-nitro benzonitrile (Elslager et al. J. Heterecyclic Chem. 9, 769–773 (1972), 8.0 g) to 10% palladium on charcoal (2.0 g) in ethanol (600 ml). Cyclohexene (10 ml) is added dropwise and the mixture refluxed 24 hr., cooled, filtered and the filtrate concentrated to dryness to afford 5-hydroxyanthranilonitrile.

EXAMPLE 70

When o-fluorobenzhydrazide is substituted for 2-furoic acid hydrazide in Example 69, 5,6-dihydro-2-(2-fluorophenyl)-9-hydroxy-[1,2,4]triazolo[1,5-c]quinazolin-5(6H) one is obtained, mp. 370°–372°, after recrystallization from dimethylformamide-water.

EXAMPLE 71

When N-carbethoxy-5-benzyloxyanthranilonitrile is substituted for N-carbethoxy-5-hydroxyanthranilonitrile in Example 69, 9-benzyloxy-5,6-dihydro-2-(2-furyl)-[1,2,4]triazolo[1,5-c]quinazolin-5(6H) one is obtained, mp. 311°–313°.

The starting urethane is prepared by reaction of N-carbethoxy-5-hydroxyanthranilonitrile with equimolar quantities of benzyl bromide and potassium carbonate in refluxing 2-butanone overnight. The mixture is concentrated to dryness and the residue recrystallized from ethyl acetate-petroleum ether to give the desired product.

EXAMPLE 72

When o-fluorobenzhydrazide is substituted for 2-furoic acid hydrazide in Example 71, 9-benzyloxy-5,6-dihydro-2-(2-furyl)-[1,2,4]triazolo[1,5-c]-quinazolin-5(6H) one is obtained, mp. 309°–311°.

EXAMPLE 73

A mixture of 3-(2-amino-5-benzyloxyphenyl)-5-(2-furyl)-1,2,4-triazole (200 mg), cyanamide (100 mg), 50% aqueous 2-propanol (20 ml) and concentrated sulphuric acid (5 drops) is heated at reflux for 66 hrs. It is concentrated to dryness at reduced pressure, triturated with water and the solid collected, washed with water and oven dried under vacuum. It is triturated with hot ethyl acetate and filtered hot. The insoluble solid is pure 9-benzyloxy-5,6-dihydro-2-(2-furyl)-5-imino-[1,2,4]triazolo[1,5-c]quinazoline, mp. 274°–276°.

The starting triazole is prepared in the following way: 9-benzyloxy-5,6-dihydro-2-(2-furyl)-[1,2,4]triazolo[1,5-c]quinazolin-5(6H) one, (Example 71, 1.0 g), sodium hydroxide (200 mg), ethylene glycol (40 ml) and water (10 ml) are heated together at 140° for 18 hrs. The mixture is concentrated to dryness at reduced pressure, water is added and the mixture adjusted to pH 7 with acetic acid. It is extracted with ethyl acetate and the organic extracts washed with water, dried over magnesium sulphate and concentrated to dryness at reduced pressure. The residue is triturated with ether, filtered and the solid dried at 60/0.1 mm for 18 hrs. to afford the pure triazole, mp. 181°–183°.

EXAMPLE 74

A mixture of 3-(2-amino-5-hydroxyphenyl)-5-(2-furyl)-1,2,4-triazole (1 g.), cyanamide (400 mg), 50% aqueous 2-propanol (100 ml) and concentrated sulphuric acid (5 drops) is stirred at reflux for 24 hr. It is evaporated to dryness at reduced pressure, triturated with water, collected and air dried. It is then triturated with 9:1 ethylacetate-methanol, collected and oven dried at reduced pressure to give pure 5,6-dihydro-2-(2-furyl)-9-hydroxy-[1,2,4]triazolo[1,5-c]quinazolin-5(6H)imine, mp. 359°–360°.

The starting triazole is prepared in the following way: A mixture of 5,6-dihydro-2-(2-furyl)-9-hydroxy-[1,2,4]triazolo[1,5-c]quinazolin-5(6H) one (Example 69, 1 g), sodium hydroxide (1 g), ethylene glycol (40 ml) and water (40 ml) is stirred under nitrogen at reflux for 18 hrs. Water is added and the pH adjusted to 7 with acetic acid. The precipitate is collected, washed several times with water and dried under high vacuum to afford the triazole of sufficient purity for the next step.

Having now fully described the invention, it will be apparent to one of ordinary skill in the art that many changes and modifications can be made thereto without departing from the spirit or scope of the invention as set forth herein.

What is claimed is:

1. A [1,2,4]triazolo[1,5-c]quinazoline-5-one compound of the formula

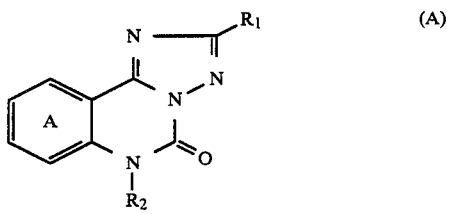

wherein
R₁ is
(a) phenyl which is unsubstituted or substituted by lower alkyl, lower alkoxy, hydroxy, halogen, or trifluoromethyl; or
(b) furyl, dihydrofuranyl, tetrahydrofuranyl, thienyl, dihydrothienyl, tetrahydrothienyl, pyranyl, pyridyl, or o-ribofuranosyl, each of which is bound to the triazoloquinazoline nucleus via a ring carbon atom, and each of which is unsubstituted or substituted by lower alkyl, hydroxy, amino, halogen, or hydroxy-lower alkyl;

$R_2$ is hydrogen or lower alkyl;

ring A is unsubstituted or substituted by a substituent selected from lower alkyl, lower alkoxy, hydroxy, halogen, trifluoromethyl, nitro, amino, $C_{1-3}$ alkylthio, $C_{1-2}$ alkylsulfonyl, $C_{1-2}$ alkylsulfinyl, and aryl-lower alkoxy, wherein said aryl portion is selected from phenyl, pyridyl, thienyl, and furyl, and said aryl portion is unsubstituted or further substituted by lower alkyl, halogen, hydroxy, nitro, amino, mono-lower alkylamino, or di-lower alkyl amino;

a tautomer thereof; and a pharmaceutically acceptable salt of said compound of formula A or said tautomer.

2. The compound of claim 1 wherein
$R_1$ is
(a) phenyl which is unsubstituted or substituted as in claim 1, or
(b) furyl, dihydrofuranyl, tetrahydrofuranyl, thienyl, dihydrothienyl, tetrahydrothienyl, pyranyl, pyridyl, or o-ribofuranosyl, each of which is unsubstituted or substituted by lower alkyl, halogen, or hydroxy;

$R_2$ is hydrogen or methyl; and ring A is unsubstituted or substituted by one to three substituents selected from lower alkyl, lower alkoxy, hydroxy, halogen and trifluoromethyl;

a tautomer thereof; and a pharmaceutically acceptable salt of said compound or said tautomer.

3. The compound of claim 1 wherein
$R_1$ is
(a) phenyl substituted by one to three substituents substituents selected from methyl, ethyl, methoxy, hydroxy, fluorine, chlorine, and trifluoromethyl; or
(b) 2-thienyl, 3-thienyl, 2-furyl, 3-furyl, 2-pyridyl, 3-pyridyl, or 4-pyridyl, each of which is unsubstituted or substituted by hydroxy, methyl, ethyl, fluorine, or chlorine;

$R_2$ is hydrogen; and ring A is substituted by one or two substituents selected from chloro, fluoro and methyl, said substituent being at position 8, position 9, or both positions 8 and 9 of said ring, and ring A having no substituent or a chloro substituent at position 7 when there is a chloro substituent at position 9;

a tautomer thereof; and a pharmaceutically acceptable salt of said compound or said tautomer.

4. The compound of claim 1 wherein $R_1$ phenyl which is unsubstituted or substituted by fluorine or chlorine in the ortho or meta position; and Ring A is unsubstituted or substituted by chlorine at the 9 position;

a tautomer thereof; and a pharmaceutically acceptable salt of said compound or said tautomer.

5. The compound of claim 1 which is 2-(2-fluorophenyl)-9-chloro[1,2,4]triazolo[1,5-c]quinazoline-5(6H)-one.

6. The compound of claim 1 which is 2-(3-fluorophenyl)-9-chloro-[1,2,4]triazolo[1,5-c]quinazoline-5(6H)-one.

7. A method of counteracting the effects of benzocarbamazepine comprising administering to a mammal in need of such administration of benzocarbamazepine countering effective amount of a compound according to claim 1 provided said compound does not have a benzyloxy group as a substituent on said ring A.

8. A method of preparing a compound of claim 1 comprising reacting a compound of the formula

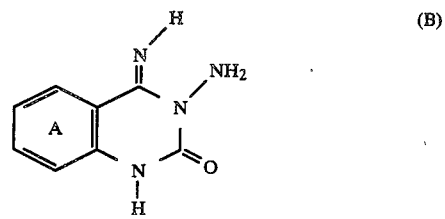

with an amidine of the formula

where ring A and $R_1$ are as defined in claim 1.

9. The method of claim 8 wherein said compound of formula B is prepared by the reaction of

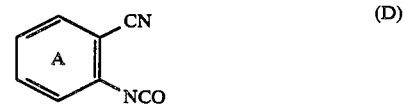

and $N_2H^4$.

10. A 5-imino[1,2,4]triazolo[1,5-c]quinazoline compound of the formula

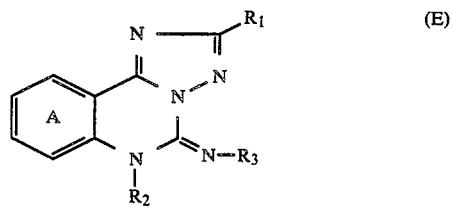

wherein
$R_1$ is
(a) phenyl which is unsubstituted or substituted by lower alkyl, lower alkoxy, hydroxy, halogen, or trifluoromethyl; or
(b) furyl, thienyl, dihydrofuranyl, tetrahydrofuranyl, dihydrothienyl, tetrahydrothienyl, pyranyl, pyridyl, or o-ribofuranosyl, each of which is bound to the triazoloquinazoline nucleus via a ring carbon atom, and each of which is unsubstituted or substituted by lower alkyl, hydroxy, amino, halogen, or hydroxy-lower alkyl;

$R_2$ is hydrogen or lower alkyl;

$R_3$ is hydrogen, lower alkyl, $C_{3-20}$ cycloalkyl, lower alkenyl, lower alkynyl, amino-lower alkyl, mono-lower alkylamino-lower alkyl, di-lower alkylamino-lower alkyl, hydroxy-lower alkyl, aryl, or aryl-lower alkyl, provided the double and triple bonds present in said $R_3$ lower alkenyl and $R_3$ lower alkynyl groups are separated from the nitrogen to which $R_3$ is attached by at least one saturated carbon atom, said aryl group in $R_3$ is phenyl, pyridyl, thienyl, or furyl, which aryl group is unsubstituted or further substituted by lower alkyl, halogen, hydroxy, nitro, amino, mono-lower alkyl-amino, or di-lower alkyl-amino; and ring A is unsubstituted or substituted by lower alkyl, lower alkoxy, hydroxy, halogen, trifluoromethyl, nitro, amino, $C_{1-3}$ alkylthio, $C_{1-2}$ alkylsulfonyl, $C_{1-2}$ alkylsulfinyl, or aryl-lower alkoxy, wherein said aryl group within said aryl-lower alkoxy is phenyl, pyridyl, thienyl, or furyl, which is unsubstituted or further substituted by lower alkyl, halogen, hydroxy, nitro, amino, mono-lower alkyl-amino, or di-lower alkyl-amino;

a tautomer thereof; and a pharmaceutically acceptable salt of said compound or said tautomer.

11. The compound of claim 10 wherein
$R_1$ is
(a) phenyl which is unsubstituted or substituted by one to three groups selected from lower alkyl, lower alkoxy, hydroxy, halogen, and trifluoromethyl; or
(b) furyl, thienyl, dihydrofuranyl, tetrahydrofuranyl, dihydrothienyl, tetrahydrothienyl, pyranyl, pyridyl or o-ribofuranosyl which is unsubstituted or substituted as in claim 10;
$R_2$ is hydrogen or lower alkyl;
$R_3$ is hydrogen, lower alkyl, amino-lower alkyl, mono-lower alkyl-amino-lower alkyl, di-lower alkyl-amino-lower alkyl, aryl, or aryl-lower alkyl wherein said aryl moiety is as defined in $R_3$ of claim 10; and
ring A is unsubstituted or substituted by one to three groups selected from lower alkyl, lower alkoxy, hydroxy, halogen and trifluoromethyl;
a tautomer thereof; and
a pharmaceutically acceptable salt of said compound or said tautomer.

12. The compound of claim 10 wherein
$R_1$ is
(a) phenyl which is unsubstituted or substituted by one to three groups selected from methyl, ethyl, methoxy, hydroxy, fluorine, chlorine, and trifluoromethyl, or
(b) 2-thienyl, 3-thienyl, 2-furyl, 3-furyl, 2-pyridyl, 3-pyridyl, or 4-pyridyl, each of which is unsubstituted or substituted by hydroxy, methyl, ethyl, fluorine, or chlorine;
$R_2$ is hydrogen or methyl;
$R_3$ is hydrogen, methyl, ethyl, or isopropyl; and
ring A is unsubstituted or substituted by one or two substituents selected from fluoro, chloro, or methyl, said substituents being at positions 8 or 9; and said ring A, if substituted at position 9 by chloro, is further substituted at position 7 by a substituent selected from hydrogen and chlorine;
a tautomer thereof; and
pharmaceutically acceptable salt of said compound or said tautomer.

13. The compound of claim 10 wherein
$R_1$ is 2-furyl;
$R_2$ and $R_3$ are each hydrogen; and
ring A is unsubstituted or substituted by chlorine at position 9.

14. The compound of claim 10 which is 2-(2-furyl)-5-imino-9-chloro-5,6-dihydro[1,2,4]triazolo[1,5-c]quinazoline.

15. A method counteracting the effects of adenosine and of treating asthma comprising administering to a mammal in need of such administration an effective amount of a compound of claim 10, a tautomer thereof, or a pharmaceutically acceptable salt of said compound or said tautomer.

16. The method of claim 15 wherein said compound is 2-(2-furyl)-5-imino-9-chloro-[1,2,4]triazolo[1,5-c]quinazoline.

17. A method of preparing a compound of claim 10 having the formula

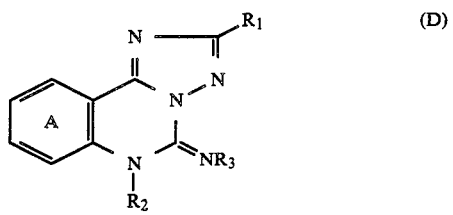
(D)

comprising reacting a compound of the formula

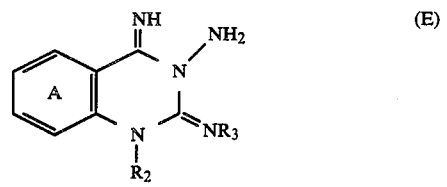
(E)

with an amidine of the formula

(F)

wherein $R_1$, $R_2$, $R_3$ and A are defined as in claim 10.

18. The method of claim 17 wherein $R_2$ is hydrogen.

19. The method of claim 17 wherein said compound of formula E is prepared by reacting a compound of the formula

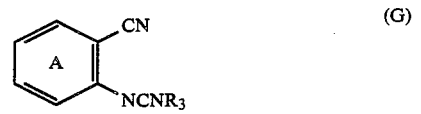
(G)

with $N_2H_4$, wherein A and $R_3$ are as defined in claim 17.

20. A method of preparing a compound of claim 10 of the formula

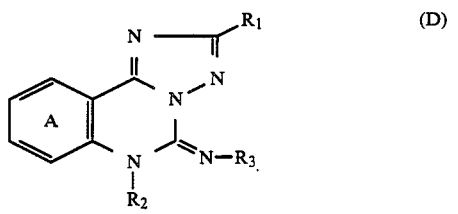
(D)

comprising reacting a compound of the formula

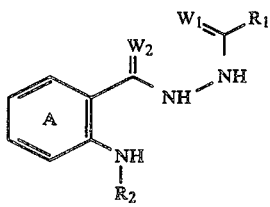

with ammonia and cyanamide; wherein one of $W_1$ and $W_2$ is NH and the other is O or NH; $R_1$, $R_2$, and A are as defined in claim 10; and $R_3$ is hydrogen.

21. A method of preparing a compound of claim 10 having the formula

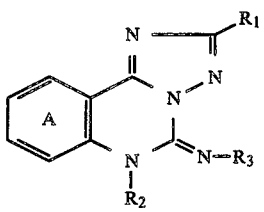

wherein $R_3$ is hydrogen, comprising reacting a compound of the formula

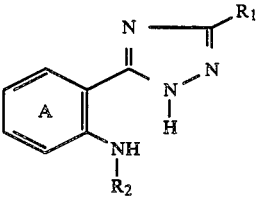

with cyanamide; $R_1$, $R_2$, and A being as defined in claim 10.

22. A pharmaceutical composition comprising
 (a) a benzodiazepine counteracting effective amount of a compound of claim 1 which does not have a benzyloxy group as a substituent on ring A; or
 (b) a benzodiazepine agonistic effective amount of a compound of claim 1 which does have a benzyloxy group as a substituent on ring A;
or a tautomer thereof or a pharmaceutically acceptable salt of said compound or tautomer;
and a pharmaceutically acceptable carrier.

23. A pharmaceutical composition comprising an adenosine antagonistic effective amount of a compound of claim 10, a tautomer thereof, or a pharmaceutically acceptable salt of said compound or tautomer; and a pharmaceutically acceptable carrier.

* * * * *